US008759486B2

(12) United States Patent
León Monzón et al.

(10) Patent No.: US 8,759,486 B2
(45) Date of Patent: Jun. 24, 2014

(54) IMMUNOMODULATORY INTERLEUKIN-2 POLYPEPTIDES AND METHODS OF TREATING MELANOMA

(75) Inventors: Kalet León Monzón, Ciudad de la Habana (CU); Tania Carmenate Portilla, Ciudad de la Habana (CU); Karina García Martínez, Ciudad de la Habana (CU); Augustín Bienvendo Lage Davila, Habana (CU); Samuel Pérez Rodríguez, Provincia Habana (CU); Diamile González Roche, Ciudad de la Habana (CU); Gabriel Márquez Perera, Ciudad de la Habana (CU)

(73) Assignee: Centro de Inmunologia Molecular, La Habana (CU)

( * ) Notice: Subject to any disclaimer, the term of this patent is extended or adjusted under 35 U.S.C. 154(b) by 0 days.

(21) Appl. No.: 13/512,429

(22) PCT Filed: Nov. 26, 2010

(86) PCT No.: PCT/CU2010/000005
§ 371 (c)(1),
(2), (4) Date: Aug. 16, 2012

(87) PCT Pub. No.: WO2011/063770
PCT Pub. Date: Jun. 3, 2011

(65) Prior Publication Data
US 2012/0315245 A1    Dec. 13, 2012

(30) Foreign Application Priority Data
Nov. 27, 2009 (CU) ................... 2009-0203

(51) Int. Cl.
C07K 14/55 (2006.01)
A61K 38/20 (2006.01)
A61K 38/00 (2006.01)

(52) U.S. Cl.
USPC ........................... 530/351; 424/85.2; 514/1.1

(58) Field of Classification Search
None
See application file for complete search history.

(56) References Cited

U.S. PATENT DOCUMENTS

| | | | |
|---|---|---|---|
| 4,853,332 | A | 8/1989 | Mark et al. |
| 4,959,314 | A | 9/1990 | Mark et al. |
| 5,116,943 | A | 5/1992 | Koths et al. |
| 5,229,109 | A | 7/1993 | Grimm et al. |
| 6,955,807 | B1 | 10/2005 | Shanafelt et al. |
| 7,105,653 | B2 | 9/2006 | Shanafelt et al. |
| 7,186,804 | B2 | 3/2007 | Gillies et al. |
| 2004/0175357 | A1 | 9/2004 | Shanafelt et al. |
| 2005/0142106 | A1 | 6/2005 | Wittrup et al. |
| 2009/0098609 | A1* | 4/2009 | Gillies et al. ............ 435/69.7 |

FOREIGN PATENT DOCUMENTS

WO    2009061853 A2    5/2009

OTHER PUBLICATIONS

Mickle, J.E. et al. Genotype-phenotype relationships in cystic fibrosis. Medical Clinics of North America, 2000, vol. 84, No. 3, p. 597-607.*
Wells, J.A. Additivity of mutational effects in proteins. Biochemistry, 1990, vol. 29, No. 17, p. 8509-8517.*
Liu David V et al: "Engineered Interleukin-2 Antagonists for the Inhibition of Regulatory T Cells", Journal of Immunotherapy, vol. 32, No. 9, Nov. 1, 2009, pp. 887-894.
Zurawski S M and Zurawski G: "Receptor antagonist and selective agonist derivatives of mouse interleukin-2", EMBO Journal, vol. 11, No. 11, Jan. 1, 1992, pp. 3905-3910.
Shanafelt A B et al: "A T-cell-selective interleukin 2 mutein exhibits potent antitumor activity and is well tolerated in vivo", Nature Biotechnology, vol. 18, No. 11, Nov. 1, 2000, pp. 1197-1202.
Litzinger Mary T et al: "IL-2 immunotoxin denileukin diftitox reduces regulatory T cells and enhances vaccine-mediated T-cell immunity", Blood, vol. 110, No. 9, Nov. 2007, pp. 3192-3201.
Wang Xinquan et al: "Structure of the quaternary complex of interleukin-2 with its alpha, beta, and gamma(c) receptors", Science (Washington D C), vol. 310, No. 5751, Nov. 2005, pp. 1159-1163.
Fernando Bazan J et al: "Unraveling the Structure of IL-2", Science (Washington D C), vol. 257, No. 5068, 1992, pp. 410-415.
Rao Balaji M et al: "High-affinity CD25-binding IL-2 mutants potently stimulate persistent T cell growth", Biochemistry, vol. 44, No. 31, Aug. 2005, pp. 10696-10701.
Ahmadzadeh, M., et al., "IL-2 administration increases CD4+CD25hiFoxp3+ regulatory T cells in cancer patients", (2006) Blood. 107, 2409-14.
Almeida, A.R., et al. Homeostasis of Peripheral CD4+ T Cells: IL-2R α and IL-2 Shape a Population of Regulatory Cells That Controls CD4 + T Cell Numbers, (2002) J Immunol. 169, 4850-60.
Blattman, J.N., et al. "Therapeutic use of IL-2 to enhance antiviral T-cell responses in vivo", (2003) Nat Med. 9, 540-7.
Boyman, O., et al., "Selective Stimulation of T Cell Subsets with Antibody-Cytokine Immune Complexes", (2006) Science. 311, 1924-1927.
Boyman, O., et al. "Potential use of IL-2/anti-IL-2 antibody immune complexes for the treatment of cancer and autoimmune disease", (2006) Expert Opin Biol Ther. 6, 1323-31.

(Continued)

Primary Examiner — Robert Landsman
Assistant Examiner — Bruce D Hissong
(74) Attorney, Agent, or Firm — Rothwell, Figg, Ernst & Manbeck, P.C.

(57) ABSTRACT

The present invention relates generally to polypeptides whose primary sequence has high sequence homology with human interleukin 2 (IL-2) with some punctual mutations in the sequence of native IL-2. The polypeptides of the present invention have an immunomodulatory effect on the immune system, which is selective/preferential on regulatory T cells. The present invention also relates to specific polypeptides whose amino acid sequence is disclosed herein. In another aspect the present invention relates to pharmaceutical compositions comprising as active ingredient the polypeptides disclosed. Finally, the present invention relates to the therapeutic use of the polypeptides and pharmaceutical compositions disclosed due to their immune modulating effect on diseases such as cancer and chronic infectious diseases.

13 Claims, 5 Drawing Sheets

(56) References Cited

OTHER PUBLICATIONS

Fishman, M., et al. "Phase II Trial of B7-1 (CD-86) Transduced, Cultured Autologous Tumor Cell Vaccine Plus Subcutaneous Interleukin-2 for Treatment of Stage IV Renal Cell Carcinoma", (2008) J Immunother. 31, 72-80.

Kamimura, D., et al. "IL-2 in Vivo Activities and Antitumor Efficacy Enhanced by an Anti-IL-2 mAB", (2006) J Immunol. 177, 306-14.

Kreitman, R.J., "Recombinant Immunotoxins Containing Truncated Bacterial Toxins for the Treatment of Hematologic Malignancies", (2009) Curr Pharm Des. 15, 2652-64.

Kuniyasu, Y., et al. "Naturally anergic and suppressive CD25+CD4+T cells as a functionally and phenotypically distinct immunoregulatory T cell subpopulation"(2000) Int Immunol. 12, 1145-55.

Lin, C.T., et al. "DNA vaccines encoding IL-2 linked to HPV-16 E7 antigen generate enahnced E7-specific CTL responses and antitumor activity", (2007) Immunol Lett. 114, 86-93.

Litzinger, M.T., et al., "IL-2 immunotoxin denileukin diftitox reduces regulatory T cells and enhances vaccine-mediated T-cell immunity" (2007) Blood. 110, 3192-201.

Malek, T.R., et al. "Tolerance, Not Immunity, Crucially Depends on IL-2", (2004) Nat Rev Immunol. 4, 665-74.

Morse, M.A.,et al., "Depletion of human regulatory T cells specifically enhances antigen-specific immune responses to cancer vaccines", (2008) Blood. 112, 610-8.

Murakami, M., "CD25+CD4+ T cells contribute to the control of memory CD8+ T cells", (2002) Proc Natl Acad Sci USA. 99, 8832-7.

Onizuka, S., et al., "Tumor Rejection by in Vivo Administration of Anti-CD25 (Interleukin-2 Receptor α) Monoclonal Antibody", (1999) Cancer Res. 59, 3128-33.

Pandiyan, P., et al., "CD4+CD25+Foxp3+ regulatory T cells induced cytokine deprivation-mediated apoptosis of effector CD4+ T cells", (2007) Nat Immunol. 8, 1353-62.

Quezada, S.A., "CTLA4 blockade and GM-CSF combination immunotherapy alters the intratumor balance of effector and regulatory T cells", (2006) J Clin Invest. 116, 1935-45.

de la Rosa, M., et al., Interleukin-2 is essential for CD4+CD25+ regulatory T cell function, (2004) Eur J Immunol. 34, 2480-8.

Kudo-Saito, C., et al., Intratumoral delivery of vector mediated IL-2 in combination with vaccine results in enhanced T cell adidity and anti-tumor activity, (2007) Cancer Immunol Immunother. 56, 1897-910.

Smith, K.A. "Interleukin-2: Inception, Impact, and Implications", (1988) Science. 240, 1169-76.

Takahashi, T. et al. "Immunologic self-tolerance maintained by CD25+CD4+ naturally anergic and suppressive T cells: induction of autoimmune disease by breaking their anergic/suppressive state", (1998) Int Immunol. 10, 1969-80.

Thornton, A.M., et al. "CD4+CD25+ Immunoregulatory T Cells Suppress Polyclonal T Cell Activation in Vitro by Inhibiting Interleukin 2 Production", (1998) J Exp Med. 188, 287-96.

Tomala, J., "In Vivo Expansion of Activated Naive CD8+ T Cells and NK Cells Driven by Complexes of IL-2 and Anti-IL-2 Monoclonal Antibody as Novel Approach of Cancer Immunotherapy",. (2009) J Immunol. 183, 4904-4912.

Wolf, M., et al. "Control of T cell hyperactivation in IL-2-deficient mice by CD4+CD25- and CD4+CD25+T cells: evidence for two distinct regulatory mechanisms", (2001) Eur J Immunol. 31, 1637-45.

\* cited by examiner

US 8,759,486 B2

IMMUNOMODULATORY INTERLEUKIN-2 POLYPEPTIDES AND METHODS OF TREATING MELANOMA

CROSS REFERENCE TO RELATED APPLICATION

This application is a 35 U.S.C. 371 National Phase Entry Application from PCT/CU2010/000005, filed Nov. 26, 2010, which claims the benefit of Cuban Patent Application No. 2009-0203 filed on Nov. 27, 2009, the disclosures of which are incorporated herein in their entirety by reference.

SCOPE OF THE INVENTION

The present invention is related to the field of biotechnology and particularly immunology. The invention is related to technical solutions with therapeutic applications for human health. It particularly relates to the therapeutic modulation of the immune system using analogs of natural molecules.

PRIOR STATE OF THE ART

Interleukin 2 (IL-2) was the first growth factor described for T cells. Since its discovery it showed a strong capacity to promote proliferation and survival of T cells in vitro (Smith, K A (1988) Science. 240, 1169-76) and to enhance T cells immune response in vivo, in the context of viral infections (Blattman, J N, et al. (2003) Nat Med 9, 540-7) or vaccines (Fishman, M., et al. (2008) J Immunother. 31, 72-80, Kudo-Saito, C., et al. (2007) Cancer Immunol Immunother. 56, 1897-910; Lin, C T, et al. (2007) Immunol Lett. 114, 86-93). However, this classical role of IL-2 as a promoter of T immune response has been questioned recently by numerous experimental data (Almeida, A. R., et al. (2002) J. Immunol. 169, 4850-60; de la Rosa, M., et al. (2004) Eur J Immunol. 34, 2480-8; Malek, T. R., et al. (2004) Nat Rev Immunol. 4, 665-74) showing that this cytokine is a homeostatic growth factor for natural regulatory T cells T CD4+CD25+FoxP3+ (Tregs).

Interleukin-2 is a major player in the mechanism by which regulatory T cells suppress the activity and expansion of other effector cells such as CD4 helpers T cells, CD8 cytotoxic T cells and NK cells. Specifically, it has been recently proposed that regulatory T cells suppress other T cells, inducing the local decrease in the levels of IL-2 (Pandiyan, P., et al. (2007) Nat Immunol. 8, 1353-62). This suppressive effect is based in: a) their ability to inhibit directly the production of IL-2 by the effector T cells that they suppresses: (Almeida, A. R., et al. (2002) J Immunol. 169, 485060; Takahashi, T., et al. (1998) Int Immunol. 10, 1969-80; Thornton, A. M., et al. (1998) J Exp Med. 188, 287-96; Wolf, M., et al. (2001) Eur J Immunol. 31, 1637-45); b) The ability to consume fast and efficiently the IL-2 in their microenvironment (Pandiyan, P., et al. (2007) Nat Immunol. 8, 1353-62); and c) Its capacity to over-express IL-2 alpha chain receptor (Kuniyasu, Y., et al. (2000) Int Immunol. 12, 1145-55), which enables them to use the IL-2 more efficiently when its concentrations are low.

Summarizing, IL-2 is a highly pleiotropic cytokine which is very significant for the biological activity of different cell populations. This property makes IL-2 an important node in the regulation of the immune response, making it an attractive and complex target for immune modulation therapies. In particular, the pleiotropic nature of the action of this cytokine, makes it very significant for the design of therapeutic strategies that modulate in a selective/preferential way the activity of this cytokine in different cell populations.

The IL-2 has been used for several years in cancer therapy. In particular, its use in high doses is an approved therapy in several countries for the treatment of melanoma and renal cell carcinoma. However, the direct use of IL-2 in patients is severely limited by is toxic effects. So much so that only 20% of eligible patients received further therapy and only 17% of patients show relevant objective response. One possible explanation for this dramatic failure in the clinical stage is that therapy with native IL-2 also stimulates regulatory T cell populations (Ahmadzadeh, M., et al. (2006) Blood. 107, 2409-14) that hamper the immunestimulation pursued with it.

Several strategies have been developed to mitigate the toxic effects of IL-2 therapy. Some of these strategies are based on the use of mutated variants of IL-2, designed to increase the capacity of signaling of this molecule mainly by means of the high affinity receptor (alpha, beta and gamma chains) and not by means of the intermediate affinity receptor (beta and gamma chains). The basic idea is to promote preferential signaling on T cell versus signaling in NK cells which are the cells believed to be responsible for the observed toxic effects. The following inventions are in the same line of work: U.S. Pat. No. 7,186,804, U.S. Pat. No. 7,105,653, U.S. Pat. No. 6,955,807, U.S. Pat. No. 5,229,109, U.S. Patent application 20050142106. It is important to note anyway that none of these inventions is related to IL-2 mutants with the capacity to differentially modulate the activity of regulatory T cells. Moreover, the mutants in these inventions are agonists of the IL-2 and not antagonist/inhibitors such as those described in this application.

Other mutated variants of the IL-2 have been created with the aim of increasing their pharmacological activity. For example, improving its folding or increasing their lifetime in blood. Among others, the following inventions are related to this line of work: U.S. Pat. No. 4,959,314, U.S. Pat. No. 5,116,943, U.S. Pat. No. 4,853,332. Again, none of these mutants has demonstrated ability to differentially modulate the activity of regulatory T cells.

Other existing inventions relate to inhibitors of the activity of IL-2, primarily for the treatment of autoimmune diseases or to prevent organ transplant rejection. Among these inventions are: U.S. Pat. No. 5,876,717, U.S. Pat. No. 5,635,597, U.S. Pat. No. 6,906,170, U.S. Pat. No. 6,168,785.

Finally, it should be referred that in the literature there are many proposals of therapeutic agents (Kreitman, R. J. (2009) Curr Pharm Des. 15, 2652-64; Litzinger, M. T., Fernando, R., Curiel, T. J., Grosenbach, D. W., Schlom, J. and Palena, C. (2007) Blood. 110, 3192-201; Morse, M. A., Hobeika, A. C., Osada, T., Serra, D., Niedzwiecki, D., Lyerly, H. K. and Clay, T. M. (2008) Blood. 112, 610-8; Onizuka, S., Tawara, I., Shimizu, J., Sakaguchi, S., Fujita, T. and Nakayama, E. (1999) Cancer Res. 59, 312833; Quezada, S. A., Peggs, K. S., Curran, M. A. and Allison, J. P. (2006) J Clin Invest. 116, 1935-45) that propose to modulate or reduce the activity of regulatory T cells in vivo. These therapeutic agents have been tested in animal models and even in patients for direct cancer therapy or to enhance the effect of vaccines. There are also some reports that propose to modulate the activity of IL-2, particularly with monoclonal antibodies (Boyman, O., Kovar, M., Rubinstein, M. P., Surh, C. D. and Sprent, J. (2006) Science. 311, 1924-1927; Boyman, O., et al. (2006) Expert Opin Biol Ther. 6, 1323-31; Kamimura, D., et al. (2006) J Immunol. 177, 306-14; Murakami, M., Sakamoto, A., Bender, J., Kappler, J. and Marrack, P. (2002) Proc Natl Acad Sci USA. 99, 8832-7; Tomala, J., Chmelova, H., Mrkvan, T., Rihova, B. and Kovar, M. (2009) J Immunol. 183, 4904-4912), to promote better or more effective immune responses. However, to the best of our knowledge there is no report in the literature, on mutated variants of the IL-2, which support the possibility of their use to modulate, selectively or preferentially the activity of regulatory T cells. In particular IL2 muteins capables of selectively/preferentially antagonize the activity of IL2 on regulatory T cells, thus affecting its function and promoting in consequence a therapeutic potentiation of immune responses.

BRIEF DESCRIPTION OF THE INVENTION

The present invention is based on the scientific finding that proves that mutant variants of IL-2 can exert a preferential inhibition on regulatory T cells. Inventors found out for the first time in in vitro experiments that mutated variants of IL-2 can substantially inhibit the activity of regulatory T cells (T CD4+CD25+FoxP3+), while hardly affecting the activation and/or proliferation of other lymphocytes with effector functions This finding provides the basis for a new strategy of immunomodulation of regulatory T cells in diseases such as cancer or chronic infections where these cells are relevant.

The present invention relates to polypeptides which share their primary sequence with human IL-2, except in the fact that several amino acids have been mutated by eliminating or substantially reducing their capacity to signal through the different forms of the IL-2 receptor These mutant variants of IL-2 maintain their ability to bind to one or more components of IL-2 receptor, and have an inhibitory activity preferentially seen on regulatory T cell populations, where they negatively modulate their function. Several specific variants of IL-2 mutants with preferential inhibitory property on regulatory T cells are protected. The invention also includes the therapeutic uses of these mutated variants, used alone or in combination with vaccines for the therapy of diseases such as cancer or chronic infections where the activity of regulatory T cells (Tregs) is relevant.

The present invention proposes a new strategy to modulate the activity of regulatory T cells in diseases in which suppression by means of these cells reduces the protective immune response, induced naturally or by vaccination. The advantages of this new therapeutic strategy over other proposals to modulate the activity of Tregs are numerous. For instance:

IL-2 mutant are virtually self proteins (except for a few mutations). This fact reduces the risk of unexpected toxicities (which are common in small size inhibitor-based strategies) or thr risk of rising an immune response against the injected drugs (as would happen in strategies such as Ontak, in which IL-2 is coupled to a foreign and toxic molecule as the diphtheria toxin).

These mutant variants of IL-2 would maintain binding affinities to the receptor of IL-2 at least of the order of the affinity of the native IL-2 (10 pM for the high affinity receptor). This affinity is difficult to achieve with strategies of inhibition of the receptor or ligand, with monoclonal antibodies or other drugs.

The small size of these mutants (15 kD) might enable them to have a high mobility and easily penetrate the tumor microenvironment. Something that is known to be complex for larger molecules such as antibodies and others.

DETAILED DESCRIPTION OF THE INVENTION

Obtaining Analog Polypeptides of IL-2.

The present invention is related to polypeptides from 100 to 500 amino acids, preferably those whose size is 140 amino acids and whose apparent molecular weight is at least 15 kD. These polypeptides maintain a high level of sequence identity with native IL2, more than 90% identity, in an area of their sequence, they include 2 to 6 mutations with respect to native IL-2.

In these positions, these polypeptides are mutated by inserting amino acid residues different to those aminoacids placed in the same position in the native IL-2. The residues that replace the original residues are selected because they have physicochemical properties very different from those in the original amino acid, residues changed from polar to apolar, from charged to uncharged, from large to small, from acid to base, among others.

The polypeptides of the present invention can also be called indistinctly immunomodulator polypeptides, analogs of IL-2 or muteins of IL-2, among others. These polypeptides are designed from the 3D structure of the IL-2 (deposited in the PDB database), introducing mutations only in the positions of the IL2 that correspond to amino acids significantly exposed to the solvent, which are identified using bioinformatics programs of the public domain such as RASMOL, SwissPDBviewer and others.

The polypeptides of this invention can be obtained in several ways, among others by protein synthesis. They could also be obtained by genetic engineering techniques, such as expressing them in inclusion bodies in bacteria such as *E. coli*. Punctual mutations at the specific positions may also be obtained by directed mutagenesis techniques by using the polymerase chain reaction.

Selection of Analog Polypeptides of IL-2 by its Biological Activity:

The polypeptides of the present invention are selected by performing in vitro or in vivo experiments to simultaneously have the following properties 1) These mutant variants of IL-2 loose or substantially reduce their signaling capacity to the different forms of the IL-2 receptor. This property can be assessed directly in in-vitro proliferation assays with cell lines, which are IL-2 dependent like CTLL2 or Kitt225, or with T lymphocytes or NK cells of murine and/or human origin. These mutants should have a stimulatory activity in these assays at least 100 times lower than that of native IL-2.

2) These mutated variants of IL-2 (muteins) maintain their ability to bind to one or more molecular components of the IL-2 receptor. This binding capacity can be assessed directly by ELISA against chains of the receptor commercially available such as alpha and beta chains of the receptor or indirectly on cell populations positive to the receptor. The recognition rates of IL-2 muteins should be comparable to those of native IL-2 in these assays 3) The mutated variants of IL-2 have an inhibitory activity of the native IL-2 activity on lymphocytes, which is preferential on regulatory T cell populations (at least in T CD4+CD25+ FoxP3+ cells). The muteins of IL-2 included in this invention are capable in a certain range of concentrations to preferentially or selectively inhibit the activity or expansion of regulatory T cells, without affecting or only minimally affecting the activity and/or expansion of other lymphocytes with effector functions such as T helper cells, cytotoxic T cells or NK cells. The preferential or selective inhibitory activity of these muteins can be evidenced in several in vitro tests, which examine the response to stimuli of mixtures of effector and regulatory populations in the presence of increasing amounts of the muteins. In the appropriate range of concentration muteins should be able to inhibit at least three times more the growth or activity of regulatory T cells than they inhibit the activity or expansion of the effector populations used in the experiment, e.g. T helper cells, cytotoxic T cells or NK cells.

This invention also includes several specific variants of IL-2 muteins (specific mutations disclosed in Table 1), which have been selected to have the properties mentioned above. These muteins include multiple aminoacids substitutions that significantly reduce their ability to stimulate murine and human lymphocytes. However, their ability to bind to alpha and beta chains of the receptor remains intact, and they gain inhibitory (antagonist) capacities of IL-2 native activity. The most significant aspect of these muteins, is that they display a marked ability for, in a certain range of concentrations, to inhibit preferentially regulatory T cells (CD4+CD25+ FoxP3+), in a culture of lymphocytes containing these cells and other effector T cells.

TABLE 1

Constructed mutants, referring to the mutation according to the numbering of the human IL2.

| Mutations | Reference name |
|---|---|
| Q22V, Q126A, I129D, S130G | M1 |
| L18N, Q126Y, S130R | M2 |
| Q13Y, Q126Y, I129D, S130R | M3 |
| L18N, Q22V, T123A, I129D, S130R | M4 |

The present invention also includes additional modifications of the type of IL-2 mutants referred to above and in particular those disclosed in Table 1. Either to increase their affinity to specific components of IL-2, but without affecting or even enhancing its preferential inhibitor properties, or to improve their in-vivo pharmacodynamics: increased life span or reduce its internalization by T cells. These additional mutations may be obtained by rational design with bioinformatics tools, or by using combinatorial molecular libraries of different nature (phage display libraries, libraries of gene expression in yeast or bacteria).

Therapeutic Application of IL-2 Analog Polypeptides;

This invention also includes pharmaceutical compositions comprising as active ingredient IL-2 muteins and its analogs, disclosed in the present invention, as well as its potential therapeutic applications with the aim of selectively modulate the activity of IL-2 on regulatory T cells. Particularly, this invention protect the use of these muteins to promote the immune response induced naturally or by vaccines in diseases such as cancer or chronic infections where regulatory T cells are particularly relevant.

For therapeutic use, the polypeptide of the present invention should be administered to a subject carrier of the disease independently or in combination with other polypeptides or other substances that facilitate or enhance its therapeutic action. The route of administration may be any of the routes of administration described by the prior art for parenteral administration of drugs. It can be preferably administered by intravenous, intramuscular, subcutaneous or intratumoral routes.

The polypeptides or fusion proteins described by the present invention can also be administered as part of a pharmaceutical composition useful in the treatment of cancer and chronic infectious diseases.

To obtain the desired therapeutic effect, the polypeptide of the present invention should be administered at doses high enough to ensure an adequate concentration in the lymph node or in the relevant peripheral site for the disease under study, it should be in the adequate range of concentrations for the mutein to show a preferential inhibitory effect on regulatory T cells. The dose referred must therefore be adjusted according to disease type and route of administration in the study. For instance in the case of tumor therapy, the dose should be adjusted until the concentrations of the mutant within the tumor and/or loco-regional lymph node are adequate to ensure a preferential inhibitory effect on regulatory T cells. The dose ranges to be explored can range from dozens of micrograms to a few milligrams per dose.

The number of administrations to be applied shall also be adjusted according to the biodistribution of the mutein in question. In general, the aforementioned effective concentrations should be maintained for a period ranging from 2 days to 30 consecutive days. Note, for example, that if the mutein is coupled to a carrier protein, the frequency of administration should be adjusted accordingly. Therapeutic action is meant by total or partial remission of the disease symptoms. For cancer, a decrease in tumor volume or an increased time to relapse will be considered, among others, as remission criteria. Finally, it should be noted that the benefits of this new therapeutic strategy as compared to other proposals to modulate the activity of Tregs would be multiple. For example:

- IL-2 mutant are virtually self proteins (except for a few mutations). This fact reduces the risk of unexpected toxicities (which are common in small size inhibitor-based strategies) or thr risk of rising an immune response against the injected drugs (as would happen in strategies such as Ontak, in which IL-2 is coupled to a foreign and toxic molecule as the diphtheria toxin).
- These mutant variants of IL-2 would maintain binding affinities to the receptor of IL-2 at least of the order of the affinity of the native IL-2 (10 pM for the high affinity receptor). This affinity is difficult to achieve with strategies of inhibition of the receptor or ligand, with monoclonal antibodies or other drugs.
- The small size of these mutants (15 kD) might enable them to have a high mobility and easily penetrate the tumor microenvironment. Something that is known to be complex for larger molecules such as antibodies and others.

EXAMPLES

Example 1

The mutants were designed computationally, from bioinformatics techniques, using as basis the reported structure of the quaternary complex of human IL-2 coupled to the receptor in line the report by Wang, X., Rickert, M. and Garcia, K. C. in *Structure of the quaternary complex of interleukin-2 with its alpha, beta, and gamma receptors*. Science, 2005. 310(5751): p. 1159-63 and energy calculation algorithms for the protein-ligand interaction in the public domain. Different variants of muteins were initially predicted to not affect the binding capacity of the alpha and beta chains of the receptor. These muteins were expressed in *E. coli* from a genetical construction in the pET28a vector including an identifying sequence of 6 histidines at the amino terminal. The muteins were purified using reverse phase (FIG. 1) obtaining with high purity (>95%). The muteins obtained were selected according to their properties in in-vitro experimental trials. Among the muteins constructed in Table 1a set of specific mutations is described that has the property of preferentially inhibit the activity of Tregs.

Example 2

The selected muteins retain the ability to bind to different components of the IL2 receptor, especially to the alpha and beta chains of the receptor. FIG. 2 shows that using ELISA tests several of the mutants specified in Table 1 maintain virtually intact its ability to bind to the alpha chain (FIG. 2) and the beta chain (FIG. 2b) of the IL-2 human receptor. FIG. 3 shows further confirmation that these mutants bind to the receptor on the cell surface (FIG. 3a) and that this union can be displaced gradually by the addition of native IL-2 (FIG. 3b).

Example 3

The selected muteins significantly reduce their ability to signal by the IL-2 receptor. FIG. 3 illustrates this fact by measuring their capacity to stimulate the growth of the CTLL2 cell line (FIG. 4a) or stimulate the differentiation of NK cells from total spleen lymphocytes (FIG. 4b). These muteins in high concentrations inhibit the activity of native IL-2, both on T lymphocytes (FIG. 5a) and on NK cells (FIG. 5b).

Example 4

The muteins selected preferentially inhibit the in vitro expansion of regulatory T cells (CD4+CD25+FoxP3+). FIG. 6 illustrates this property for one of the mutants in table 1, particularly it is shown that in a lymphocyte cell culture where there is a mixture of effector and regulatory T cells stimulated with anti-CD3 antibodies, the addition of intermediate doses of muteins substantially inhibits CD4+FoxP3+ proliferation without significantly affecting the expansion of CD4+FoxP3− effector populations.

Example 5

The selected muteins are sequestered preferentially by the regulatory T cells in a culture, reducing their ability to affect the activity of effector T cells. These muteins inhibit the signaling (stimulation) mediated by the IL-2 produced endogenously by CD4+CD25−FoxP3− helper T cell populations purified and stimulated with anti-CD3 antibodies. However, the addition of increasing amounts of CD4+CD25+FoxP3+ regulatory T cells to these cultures, paradoxically reduces the inhibition mediated by the mutant on T effector populations (FIG. 7). This effect is explained by the ability of the muteins described to preferentially inhibit the activity of IL-2 on T regulatory populations. The presence of regulatory T cells even in small quantities directs the activity of the mutants to these cells, thus reducing the suppressive activity of the mutein in the effector population.

Example 6

The selected muteins show antitumoral activity on a murine model of transplantable tumor. FIG. 8 shows the described property for one of the mutein from table 1. The mutein was evaluated on a primary tumor model with melanoma MB16F10 cell line, implanted subcutaneously on the right flank. FIG. 8 shows the reduction of tumoral volume on mice treated with the mutein compared with control group treated with PBS. Besides, a control group, treated with the anti CD25 monoclonal antibody (MAb) was included, showing that the experimental system is sensible to Tregs cell depletion.

BRIEF DESCRIPTION OF THE FIGURES

FIG. 6b shows the levels of proliferation in effector cell measured by CFSE dilution, for different amounts of regulatory cells in culture. As can be seen in the absence of Tregs, the presence of muteins substantially affect the proliferation of effector cells (inhibitory effect), but as Tregs are added, the proliferation of effector T cells recovers, since Tregs preferentially sequester the mutein releasing effector cells of its inhibitory effect.

Figure 1:
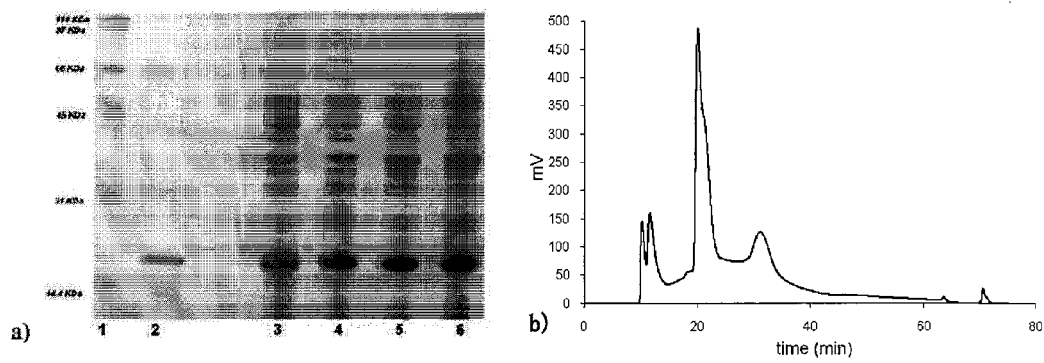
FIG. 1. Production and purification of mutated variants of human IL-2. a: Western blot showing the expression of some mutated variants and control native IL-2 in *E. coli* strains transfected with the performed gene construction; b: Example of a typical purification profile obtained using reverse phase purification.
Figure 2:
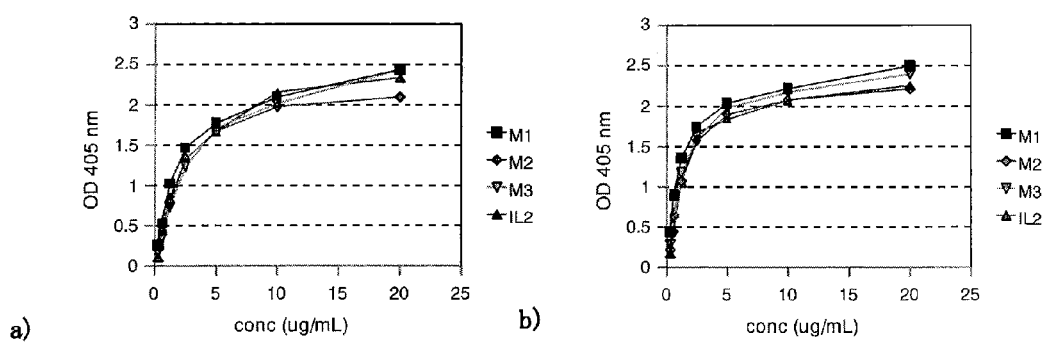
FIG. 2. Evaluation by ELISA of the recognition of the alpha (a) and beta (b) chains of IL-2 receptor by several of the muteins mentioned in table 1. Native IL-2 is used as positive control. As can be seen, all tested muteins maintain recognition rates comparable to those of native IL-2.
Figure 3:
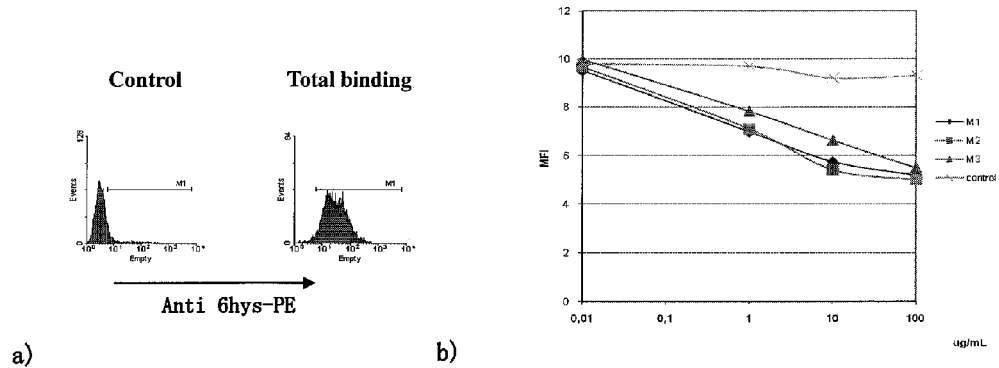
FIG. 3. Flow cytometry assessment of the ability of several of the muteins mentioned in Table 1 to bind to IL-2 receptor on the surface of the cells. Specially to murine CTLL2 cell line. Both the muteins and the control of the native IL-2 on the surface of the cells were detected with an anti-6-His-PE antibody that recognizes the head of the histidine which is included in the genetic construction of these molecules. a): Histograms showing the levels of direct binding detected. b) Reduction of the muteins binding to the cells, measured by the reduction in mean intensity of the fluorescence detected, caused by the addition of increasing amounts of native IL-2 (a variant of this molecule has no histidine head and does not interfere with the staining).
Figure 4:
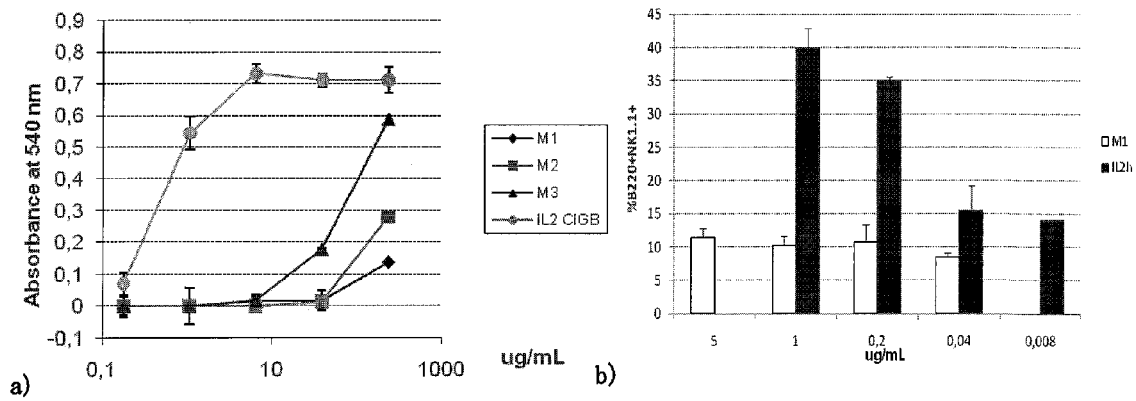
FIG. 4. Evaluation of the signaling capacity of several of the muteins mentioned in Table 1. a): The activity of the muteins was evaluated in a proliferation assay of CTLL2 cell line measured by a colorimetric assay using MTT. b): The muteins were also evaluated in a differentiation test of NK1.1+ cells from total mouse splenocytes. In both cases we compare the ability to stimulate of the muteins against a control of native IL-2 that is produced in exactly the same experimental system (the same genetic construction, *E. coli* producing strain, purification system). Similar results to those shown in FIG. 3a are obtained with Kitt225 cell line, where the system of receptors is human.
Figure 5:
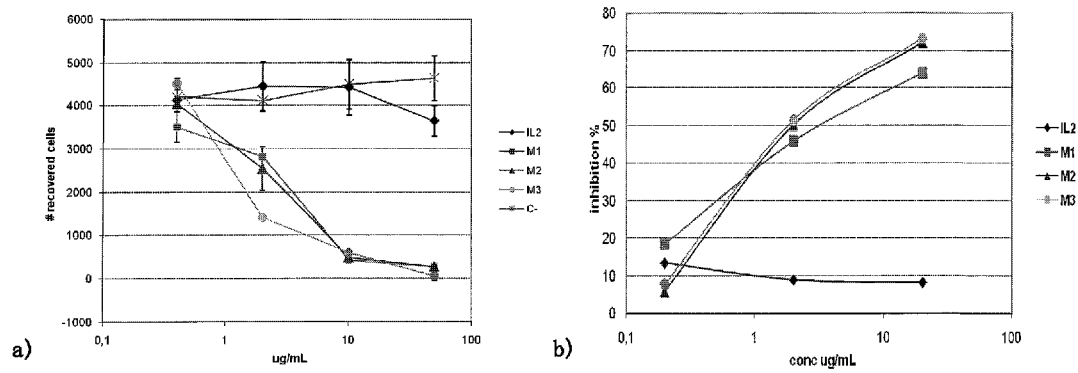
FIG. 5. Evaluation of the ability of several of the muteins mentioned in Table 1 to inhibit the in vitro activity of native IL-2. a: Inhibition of total ganglia lymphocyte proliferation stimulated with an anti-CD3 monoclonal antibody (clone 2C11 at 10 µg/mL) by increasing concentrations of muteins. b. Inhibition of the differentiation of NK1.1+ cells from total mouse splenocytes stimulated with 500 IU/mL of native IL-2, by adding increasing amounts of muteins in the culture.
Figure 6:
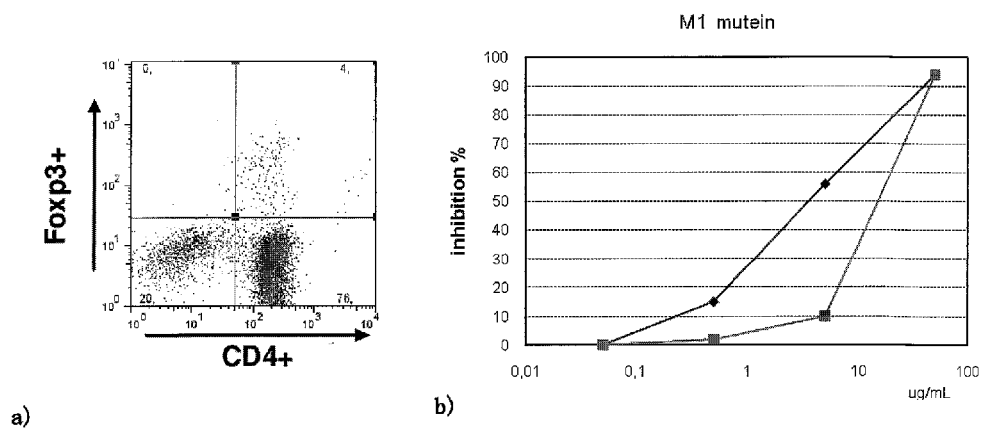
FIG. 6. Evaluation of the ability of muteins to preferentially inhibit CD4+Foxp3+ lymphocytes. The mouse lymph node lymphocytes were stimulated in vitro with an anti-CD3 monoclonal antibody (clone 2C11 at 10 µg/mL) in the presence of the indicated amounts of the M1 mutein (as referenced in Table 1). After 72 hours of culture it was determined by flow cytometry, using reference beads, the number of living CD4+Foxp3+ regulatory and CD4+Foxp3 effector lymphocytes. The graph in a shows the basic staining in flow cytometry used to differentiate regulatory and effector cell populations. The graph in b shows the levels of inhibition of the proliferation induced by different amounts of the mutein added. This inhibition is calculated based on the number of live cells recovered in the absence of the mutein. As shown in b there is an intermediate range of concentrations of M1 mutein in which the inhibition of CD4+FoxP3+ regulatory population is much more significant than for CD4+FoxP3− helper or effector T cells.
Figure 7:
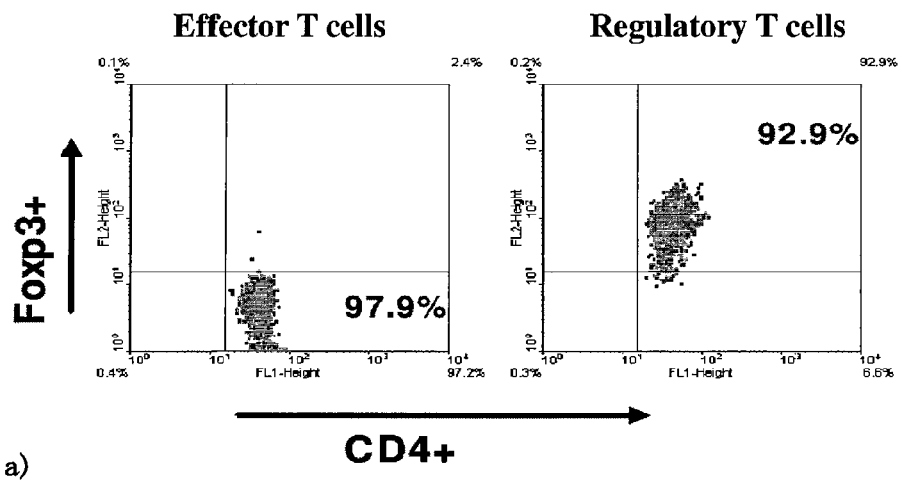
FIG. 7. Evaluation of the ability of regulatory T cells to preferentially sequester the IL-2 muteins designed, releasing effector T cells with an inhibitory effect on them. Effector T cells CD4+CD25−FoxP3− were purified using magnetic beads labeled with CFSE and placed in culture coupled some in the presence and some in the absence of muteins (M1 mutein graph, two different concentrations 10 µg/mL and 5 µg/mL) and stimulated with anti-CD3 antibodies (clone 2C11, 10 µg/mL) and anti-CD28 (clone 37.51, 10 µg/mL). Different amounts of purified regulatory T cells (CD4+ CD25+FoxP3+), were added to these cultures. The graph 6a shows high levels of purity (92% Tregs and 97% for effector T cells) achieved with magnetic beads separation.
Figure 7:
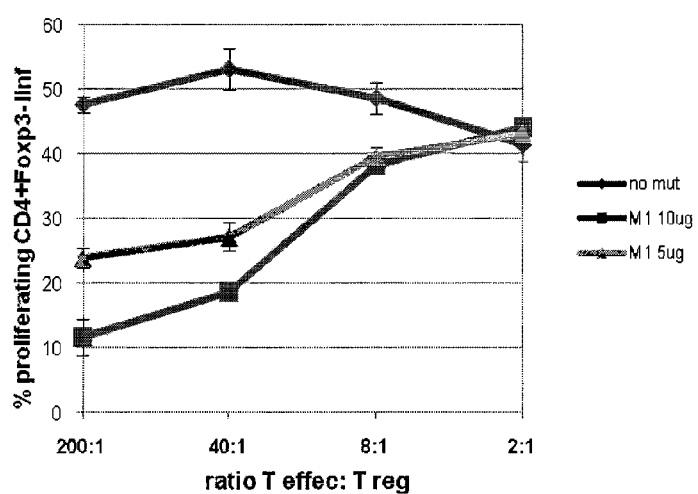
Figure 8:
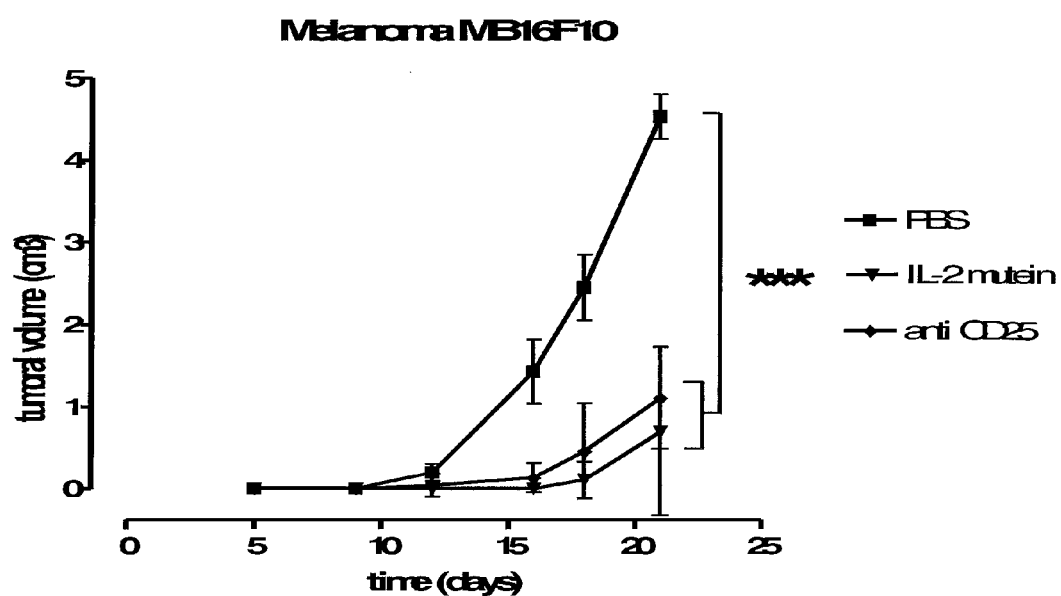
FIG. 8. Evaluation of direct antitumoral effect of IL-2 muteins using the primary tumor model with melanoma MB16F10 tumoral cell line. 12 C57BL6 mice were used, distributed in three groups of four mice each. All treatments were given subcutaneously from day −5 to day 0. Group 1 received 200 µL of PBS, group 2 received 100 µg of anti CD25 MAb and group 3 received 200 µg of IL-2 mutein. On day cero, all mice received 250 000 cells on the right flank. Tumor volume was measured every two days until day 30. Data was analyzed using ANOVA test and multiple comparison Bonferroni's test. IL-2 mutein as anti CD25 MAb caused a significant delay on tumor growth ($p<0.001$).

The invention claimed is:

1. An isolated immunomodulatory polypeptide derived from interleukin-2 (IL-2), which consists of several point mutations in respect to the sequence of human IL-2 and has the property of inhibiting IL-2 activity on regulatory T cells in vitro, wherein the polypeptide is selected from the group consisting of (i) said polypeptide consisting of mutations Q22V, Q126A, I129D, and S130G; (ii) said polypeptide consisting of mutations L18N, Q126Y and S130R; (iii) said polypeptide consisting of mutations Q13Y, Q126Y, I129D and S130R; (iv) said polypeptide consisting of mutations L18N, Q22V, T123A, I129D and S130R.

2. The polypeptide of claim 1 wherein said polypeptide has the ability to preferentially inhibit regulatory T cells in vivo.

3. A fusion protein comprising the immunomodulatory polypeptide of claim 1 coupled to a carrier protein.

4. The fusion protein of claim 3 wherein the carrier protein is albumin.

5. The fusion protein of claim 3 wherein the carrier protein is the Fc region of human immunoglobulin.

6. A pharmaceutical composition useful in the treatment of melanoma, comprising as an active ingredient the polypeptide of claim 1.

7. A pharmaceutical composition useful in the treatment of melanoma, comprising as an active ingredient the fusion protein of claim 3.

8. A pharmaceutical composition useful in the treatment of melanoma, comprising as an active ingredient the fusion protein of claim 4.

9. A pharmaceutical composition useful in the treatment of melanoma, comprising as an active ingredient the fusion protein of claim 5.

10. A method of treating melanoma in a patient in need of such treatment, comprising administering an effective amount of the polypeptide of claim 1.

11. A method of treating melanoma in a patient in need of such treatment, comprising administering an effective amount of the fusion protein of claim 3.

12. A method of treating melanoma in a patient in need of such treatment, comprising administering an effective amount of the fusion protein of claim 4.

13. A method of treating melanoma in a patient in need of such treatment, comprising administering an effective amount of the fusion protein of claim 5.

* * * * *